(12) United States Patent
Holmberg et al.

(10) Patent No.: US 7,591,786 B2
(45) Date of Patent: Sep. 22, 2009

(54) DOCK FOR CONNECTING PERIPHERAL DEVICES TO A MODULAR DIAGNOSTIC ULTRASOUND APPARATUS

(75) Inventors: Randy T. Holmberg, Bothell, WA (US); Blake W. Little, Bothell, WA (US); Steven M. Bunce, Sedro Woolley, WA (US)

(73) Assignee: SonoSite, Inc., Bothell, WA (US)

( * ) Notice: Subject to any disclaimer, the term of this patent is extended or adjusted under 35 U.S.C. 154(b) by 1038 days.

(21) Appl. No.: 10/356,401

(22) Filed: Jan. 31, 2003

(65) Prior Publication Data

US 2004/0150963 A1 Aug. 5, 2004

(51) Int. Cl.
*A61B 8/00* (2006.01)

(52) U.S. Cl. .................. 600/437; 600/459; 710/303; 710/304

(58) Field of Classification Search ............... 600/437, 600/459; 73/584, 628, 632; 361/686, 681; 710/303
See application file for complete search history.

(56) References Cited

U.S. PATENT DOCUMENTS

| | | | | |
|---|---|---|---|---|
| 2,817,793 | A | * | 12/1957 | Tudbury et. al. ............ 361/33 |
| 4,688,579 | A | | 8/1987 | Inahara |
| 4,715,385 | A | | 12/1987 | Cudahy et al. |
| 4,895,161 | A | | 1/1990 | Cudahy et al. |
| 4,907,118 | A | * | 3/1990 | Hames ..................... 361/56 |
| 5,163,451 | A | * | 11/1992 | Grellas .................... 128/898 |
| 5,205,175 | A | | 4/1993 | Garza et al. |
| 5,295,485 | A | | 3/1994 | Shinomura et al. |
| 5,318,027 | A | * | 6/1994 | Fukui ...................... 600/437 |
| 5,323,291 | A | | 6/1994 | Boyle et al. |
| 5,347,425 | A | | 9/1994 | Herron et al. |
| 5,375,604 | A | | 12/1994 | Kelly et al. |
| 5,457,784 | A | * | 10/1995 | Wells et al. .................. 710/9 |
| 5,460,547 | A | | 10/1995 | Belt et al. |
| 5,505,203 | A | * | 4/1996 | Deitrich et al. ............ 600/437 |
| 5,568,359 | A | | 10/1996 | Cavello et al. |

(Continued)

FOREIGN PATENT DOCUMENTS

DE 2003/10224234 1/2003

(Continued)

OTHER PUBLICATIONS

Logiq Book [GE Medical Systems website], [retrieved on Apr. 3, 2003] Retrieved from General Electric Medical Systems website using Internet<URL:http://www.gemedicalsystems.com/rad/us/products/logiqbook/logiqbook_intro.3.html (total of 3 pages).

(Continued)

*Primary Examiner*—Brian Casler
*Assistant Examiner*—Parikha S Mehta
(74) *Attorney, Agent, or Firm*—Fulbright & Jaworski, L.L.P.

(57) ABSTRACT

The present invention describes a system for use with a core module for diagnostic ultrasound, the system comprising at least one core module having a housing, system electronics package and a I/O port and one or more docking station(s) in electronic communication with a plurality of peripheral devices, the docking station capable of releasable connection to the core module. The invention further details the individual modular components of the system, being a receptacle connector, a docking station, a multiple transducer adaptor and a mobile docking station.

28 Claims, 8 Drawing Sheets

U.S. PATENT DOCUMENTS

| | | | |
|---|---|---|---|
| 5,590,658 | A | 1/1997 | Chiang et al. |
| 5,603,323 | A | 2/1997 | Pflugrath et al. |
| 5,604,663 | A * | 2/1997 | Shin et al. .................. 361/686 |
| 5,627,974 | A * | 5/1997 | Watts et al. ................. 710/304 |
| 5,640,953 | A | 6/1997 | Bishop et al. |
| 5,640,960 | A | 6/1997 | Jones et al. |
| 5,682,902 | A | 11/1997 | Herleikson |
| 5,685,314 | A | 11/1997 | Geheb et al. |
| 5,687,387 | A | 11/1997 | Endejan et al. |
| 5,687,717 | A | 11/1997 | Halpern et al. |
| 5,715,823 | A | 2/1998 | Wood et al. |
| 5,752,917 | A | 5/1998 | Fuchs |
| 5,758,649 | A | 6/1998 | Iwashita et al. |
| 5,795,297 | A * | 8/1998 | Daigle ........................ 600/447 |
| 5,839,442 | A | 11/1998 | Chiang et al. |
| 5,851,186 | A | 12/1998 | Wood et al. |
| 5,865,650 | A * | 2/1999 | Marian et al. ............... 439/638 |
| 5,872,557 | A | 2/1999 | Wiemer et al. |
| 5,888,087 | A | 3/1999 | Hanson et al. |
| 5,891,035 | A | 4/1999 | Wood et al. |
| 5,897,498 | A | 4/1999 | Canfield, II et al. |
| 5,938,607 | A | 8/1999 | Jago et al. |
| 5,971,923 | A | 10/1999 | Finger |
| 5,982,614 | A * | 11/1999 | Reid .......................... 361/686 |
| 6,063,030 | A | 5/2000 | Vara et al. |
| 6,117,085 | A | 9/2000 | Picatti et al. |
| 6,135,801 | A | 10/2000 | Helot et al. |
| 6,142,940 | A | 11/2000 | Lathbury et al. |
| 6,171,244 | B1 | 1/2001 | Finger et al. |
| 6,178,474 | B1 * | 1/2001 | Hamano et al. ............. 710/303 |
| 6,183,417 | B1 | 2/2001 | Geheb et al. |
| 6,190,326 | B1 | 2/2001 | McKinnon et al. |
| 6,206,578 | B1 | 3/2001 | Shin et al. |
| 6,241,673 | B1 | 6/2001 | Williams |
| 6,251,073 | B1 | 6/2001 | Imran et al. |
| 6,312,381 | B1 | 11/2001 | Knell et al. |
| 6,358,204 | B1 | 3/2002 | Finger et al. |
| 6,364,839 | B1 | 4/2002 | Little et al. |
| 6,381,484 | B1 * | 4/2002 | Ayanruoh ................... 600/407 |
| 6,407,335 | B1 | 6/2002 | Franklin-Lees et al. |
| 6,409,660 | B1 | 6/2002 | Sjoqvist |
| D461,814 | S | 8/2002 | Felix et al. |
| 6,436,039 | B1 | 8/2002 | Lannutti et al. |
| 6,440,072 | B1 | 8/2002 | Schuman et al. |
| D462,446 | S | 9/2002 | Felix et al. |
| 6,443,543 | B1 * | 9/2002 | Chiang .................... 312/223.3 |
| 6,468,212 | B1 | 10/2002 | Scott et al. |
| 6,468,213 | B1 | 10/2002 | Knell et al. |
| 6,471,651 | B1 | 10/2002 | Hwang et al. |
| 6,475,146 | B1 * | 11/2002 | Frelburger et al. .......... 600/437 |
| D467,002 | S | 12/2002 | Felix et al. |
| 6,488,625 | B1 | 12/2002 | Randall et al. |
| 6,493,220 | B1 | 12/2002 | Clark et al. |
| 6,497,664 | B1 | 12/2002 | Randall et al. |
| D469,539 | S | 1/2003 | Felix et al. |
| 6,508,763 | B1 | 1/2003 | Urbano et al. |
| D469,877 | S | 2/2003 | Felix et al. |
| 6,517,491 | B1 | 2/2003 | Thiele et al. |
| 6,524,244 | B1 | 2/2003 | Knell et al. |
| 6,561,979 | B1 | 5/2003 | Wood et al. |
| 6,569,097 | B1 | 5/2003 | McMorrow et al. |
| 6,569,102 | B2 | 5/2003 | Imran et al. |
| 6,575,908 | B2 | 6/2003 | Barnes et al. |
| 6,593,528 | B2 | 7/2003 | Franklin-Lees et al. |
| 6,595,921 | B1 | 7/2003 | Urbano et al. |
| 6,618,206 | B2 | 9/2003 | Tarakci et al. |
| 6,629,928 | B1 | 10/2003 | Dolan et al. |
| 6,644,748 | B2 * | 11/2003 | Tholkes et al. ......... 297/423.12 |
| 6,661,648 | B2 * | 12/2003 | Dayley ....................... 361/683 |
| 6,663,567 | B2 | 12/2003 | Ji et al. |
| 6,669,634 | B2 | 12/2003 | Amemiya et al. |
| 6,685,645 | B1 | 2/2004 | McLaughlin et al. |
| 6,716,167 | B1 | 4/2004 | Henderson et al. |
| 6,721,178 | B1 | 4/2004 | Clark et al. |
| 6,732,218 | B2 * | 5/2004 | Overtoom et al. ........... 710/313 |
| 6,733,455 | B2 | 5/2004 | Mo et al. |
| 6,773,399 | B2 | 8/2004 | Xi et al. |
| 6,852,081 | B2 | 2/2005 | Sumanaweera et al. |
| 6,866,631 | B2 | 3/2005 | McLaughlin et al. |
| 6,866,632 | B1 | 3/2005 | Chou et al. |
| 6,896,658 | B2 | 5/2005 | Ji et al. |
| 6,936,008 | B2 | 8/2005 | Tarakci et al. |
| 6,969,352 | B2 * | 11/2005 | Chiang et al. ............... 600/437 |
| 6,980,419 | B2 | 12/2005 | Smith et al. |
| 7,009,840 | B2 | 3/2006 | Clark et al. |
| 7,037,264 | B2 | 5/2006 | Poland |
| 7,141,020 | B2 | 11/2006 | Poland et al. |
| 2002/0016545 | A1 | 2/2002 | Quistgaard et al. |
| 2002/0103435 | A1 | 8/2002 | Mault |
| 2002/0143256 | A1 | 10/2002 | Wing et al. |
| 2002/0173721 | A1 | 11/2002 | Grunwald et al. |
| 2003/0004414 | A1 | 1/2003 | McLaughlin et al. |
| 2003/0013959 | A1 | 1/2003 | Grunwald et al. |
| 2003/0013965 | A1 | 1/2003 | Quistgaard et al. |
| 2003/0013966 | A1 | 1/2003 | Barnes et al. |
| 2004/0150963 | A1 | 8/2004 | Holmberg et al. |
| 2004/0152982 | A1 | 8/2004 | Hwang et al. |
| 2004/0158154 | A1 | 8/2004 | Hanafy et al. |
| 2005/0131294 | A1 | 6/2005 | Ji et al. |
| 2006/0013966 | A1 | 1/2006 | Koninckx et al. |
| 2006/0098864 | A1 | 5/2006 | Ziel |

FOREIGN PATENT DOCUMENTS

| | | |
|---|---|---|
| JP | 8275926 | 10/1996 |
| JP | 8280635 | 10/1996 |
| WO | WO-94/14128 | 6/1994 |
| WO | WO 00/66003 | * 11/2000 |
| WO | WO 01/13796 | 3/2001 |
| WO | WO 2004/080364 | 9/2004 |

OTHER PUBLICATIONS

International Partial Search Report issued for PCT/US2004/002423, dated Oct. 5, 2004.

English-Translated Chinese Office Action issued for Chinese Patent Application 200480006334.4; Dated Jan. 4, 2008; 11 pages.

Plaintiff and Counterclaim Defendant Sonosite's Preliminary Invalidity Contentions, United States District Court, Case SACV07-222AG (FFMx), dated Sep. 11, 2007, pp. 1-4, including Exhibits B-M, pp. 1-368.

* cited by examiner

DOCK FOR CONNECTING PERIPHERAL DEVICES TO A MODULAR DIAGNOSTIC ULTRASOUND APPARATUS

CROSS-REFERENCES TO RELATED APPLICATIONS

This application contains common subject matter with U.S. patent application Ser. No. 10/356,335 filed concurrently with the present application, the contents of which are herein incorporated by reference.

BACKGROUND OF THE INVENTION

1. Field of the Invention

The present invention relates to diagnostic ultrasound equipment. More particularly the present invention describes a modular system having a mobile core module for data processing, beamforming and system operations, and additional modules capable of connecting to the core module to provide additional features and connectivity to peripheral devices needed in diagnostic ultrasound procedures.

2. Description of the Background Art

Modern ultrasound diagnostic systems are large, complex instruments. Today's premium ultrasound systems, while mounted in carts for portability, continue to weigh several hundred pounds. In the past, ultrasound systems such as the ADR 4000 ultrasound system, produced by Advanced Technology Laboratories, Inc., were smaller desktop units about the size of a personal computer. However such instruments lacked many of the advanced features of today's premium ultrasound systems such as color Doppler imaging and three dimensional display capabilities.

The judicious use of power and signal processing on ASIC devices has enabled smaller system to push past the feature limitations in smaller older systems that employed mechanical transducers or analog chip sets. Digital beam forming and advanced processing is now available on smaller systems such as the SonoHeart Elite, by SonoSite, Inc., and common assignee of the present invention. The success of the handheld device has spawned competitive products that are beginning to offer more advanced features. However, the use of a small handheld requires a trade off in the form of display size and battery life. Cart based units provide users with the luxury of full sized CRT monitors, as well as a host of peripheral devices at the ready. Hand held devices offer portability, but are restricted to the features built in to their chassis. Some hand held devices are offered in combination with an interface to added peripherals through a cart add on, however this increases the cost of the device and requires a user to buy specialized equipment from the manufacturer of the hand held.

Thus, there remains a need for a diagnostic ultrasound instrument which provides the advantages of light weight mobility, combined with advanced functionality traditionally restricted to larger cart based system.

There is also a need for a more economical diagnostic ultrasound system that will allow small users and institutions to purchase ultrasound units that have the capacity the user or institution requires without having to pay the expense of additional features the user or institution will not use.

There further remains a need for a device that is portable, and remains highly resistant to shock damage from being dropped or jostled during transport from place to place.

BRIEF SUMMARY OF THE INVENTION

The present invention relates to a modular diagnostic ultrasound apparatus for use in multiple environments. In a first embodiment a modular diagnostic ultrasound apparatus is disclosed comprising a core unit, a system electronics package and at least one I/O port. The core unit is a housing containing the system electronics package. The system electronics package having one or more concatenated filters, including a front end transmit/receive circuit, a processor, a back end circuit for scan conversion, a system clock and a programmable system memory device. There is also at least one I/O port connected to the front end and the back end of the system electronics package and extending through the core unit housing wherein all system data processing information is transmitted or received through the at least one I/O port.

In a second embodiment, a modular diagnostic ultrasound apparatus contained within a clamshell style enclosure weighing less than 10 pounds (4.5 kg), said enclosure further comprising: a bottom unit having a system electronics package, a battery, a plurality of user interface elements positioned substantially on a top surface of said bottom unit, at least one I/O port connector in electronic communication with said system electronics package and extending through the enclosure; a top unit hingedly connected to said bottom unit, consisting of a video display screen; and an aperture for receiving a transducer connector, said aperture being positioned substantially on the underside of the bottom unit.

In another aspect of the present invention, a mini-dock for connecting peripheral devices to a modular diagnostic ultrasound apparatus is disclosed, the mini-dock comprising: a receptacle housing; a plurality of peripheral device ports, mounted in the receptacle housing, each peripheral device port connected to one or more individual electrical connector(s) for electrical communication with a receptacle; and a receptacle for releasably mating with an I/O port of the modular diagnostic ultrasound apparatus, the receptacle capable of electronic communication with said plurality of peripheral device ports.

Another aspect of the present invention is a docking station for connecting a plurality of peripheral devices to a modular diagnostic ultrasound apparatus, the docking station comprising: a mini-dock having a housing, a plurality of peripheral device ports in electronic communication with a receptacle, the mini-dock being fixedly attached to a base; a base having a means for guiding a modular diagnostic ultrasound apparatus into alignment with the mini-dock, and a means for securing the modular diagnostic ultrasound apparatus to the mini-dock; and a power supply incorporated within the base and in electronic communication with the mini-dock such that electrical power can be fed from the power supply to the modular ultrasound apparatus through the mini-dock.

Another aspect of the modular diagnostic ultrasound apparatus is a multi-transducer connector module (multi-tap module) comprising a housing having a raised relief connector for mating with an aperture for a transducer connector on a modular diagnostic ultrasound apparatus, the multi-transducer connector having a plurality of recess connectors for fittingly engaging a plurality of transducer connectors (each using a raised relief connector adaptor), the housing having a switch for each recess connector by which an operator can select which transducer is connected to the ultrasound device to be used at any particular moment. The switch for selecting which transducer to be used may either be an electromechanical switch, or a software implementation of a switch controlled through the user interface of the modular diagnostic ultrasound apparatus.

Still another aspect of the present invention is a mobile docking station for use with a modular diagnostic ultrasound apparatus comprising: a base having a plurality of castors wherein at least one said castor is capable of locking; a tower mounted on said base; a docking station located substantially near the top of the tower, the docking station capable of releasably receiving a modular diagnostic ultrasound apparatus; and a recesses for a plurality of peripheral devices, ergonomically positioned within said tower to allow a user convenient operation of the modular diagnostic ultrasound apparatus and a number of peripheral devices in the course of a diagnostic ultrasound scan procedure.

The modular diagnostic ultrasound apparatus also includes a system for diagnostic ultrasound examinations comprising a modular diagnostic ultrasound apparatus having an aperture for receiving a transducer connector, a sample data beamformer and signal processing electronics combined and at least one I/O port, the modular ultrasound apparatus being releasably connected to a mini-dock; a mini-dock having a plurality of peripheral device ports and a receptacle for releasably engaging said I/O port; and a mobile docking station for the modular diagnostic ultrasound apparatus, a tower, a plurality of recesses for peripheral devices and base; wherein the modular diagnostic ultrasound apparatus may operate as a portable diagnostic ultrasound device when removed from said system, or as a cart style ultrasound system when in electronic communication with said mini-dock.

DETAILED DESCRIPTION OF THE INVENTION

The focus of the present invention lies in a modular ultrasound system having a core module having the essential ultrasound processor functions, and a series of additional modules which, when combined with the core module, provide expanded capability and utility to the core module. The following description gives both the principle embodiment and alternative embodiments of the invention. Use of certain terms in the disclosure warrant clarification before an in depth discussion can occur.

The invention presented here is for an ultrasound device to be principally used for diagnostic purposes. However the term diagnostic should not be misconstrued to be read as being for non-therapeutic purposes. We use the term diagnostic to mean providing high quality imaging, as is characteristic of diagnostic imaging devices in the medical ultrasound industry. Because the present invention can provide images for use in biopsy procedures, Peripherally Inserted Central Catheter (PICC) lines and other procedures, the use of the ultrasound device herein is not purely for diagnosis of diseases. However, we specifically disclaim any use of the present invention for a purely therapeutic purpose, such as ablative ultrasound, thermal heating (as in the treatment of hypothermia) or mechanical tissue disruption, such as the generation of cavitation effects. The diagnostic ultrasound device of the present invention runs with the same power and frequency of devices used for diagnostic imaging, or therapies using diagnostic imaging—the device itself is not used as the source of therapy.

A focal point of the invention is the communication ability of the core module to the various other modules that comprise the system of the invention. Thus the core module has a single I/O port in its preferred embodiment sometimes referred to as the plug. The plug is a multi-pin electronic communication adaptor for matingly engaging a receptacle. The receptacle is a device with a corresponding pin set to match up the plug, and read data from the core module and sort it out to a variety of other devices that are in electronic communication with the receptacle. In alternative embodiments, there may be multiple I/O ports and a plug. The plug retains its function in all embodiments of the present invention, though electronic communication with additional module and components may be achieved through dedicated I/O ports. Any port in addition to the plug is a dedicate I/O port designed to receive input, or transmit output to a particular device. Likewise, in alternative embodiments of modules with a receptacle, there are no other I/O ports involved except the receptacle designed to mate with and communicate with the plug.

The core unit has a system electronics that should be understood to be the central processing core of the ultrasound device and the ultrasound engine. It can be thought of as an ultrasound motherboard. The system electronics of the core module, both in the preferred embodiment, and alternative embodiments, has the capacity to recognize and drive a group of transducer arrays such that a single core module can be connected with a plurality of transducers and perform all types of ultrasound procedures the transducers are designed for.

Figure 1A:
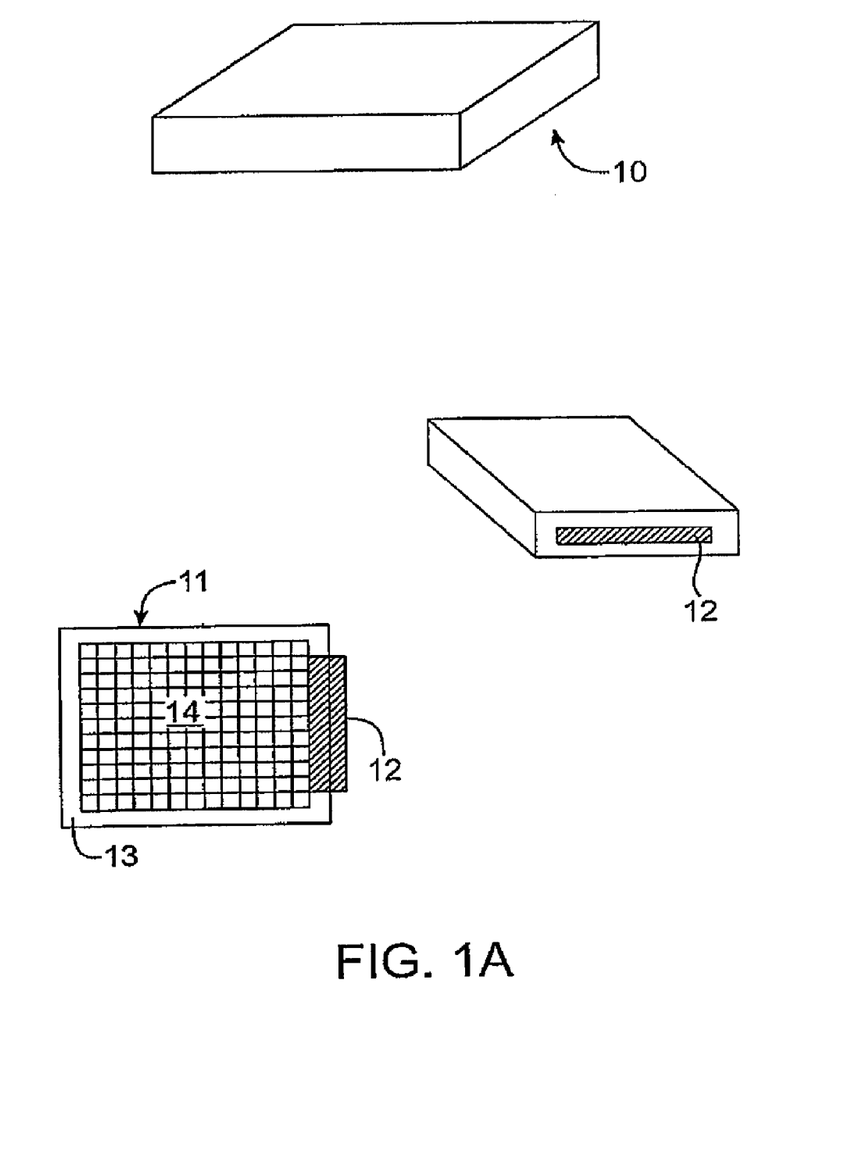
FIG. 1A illustrates in block diagram form the architecture of a hand held ultrasound system.

Turning now to FIG. 1A, a core module 10 for an ultrasound system is illustrated having system electronics 14 allowing the core module 10 to operate as a data processing and signal processing unit for a modular ultrasound system 60. The core module 10 comprises a housing 11 having the system electronics 14 mated to an I/O connector (plug) 12. A gap space 13 exists between the system electronics 14 and housing 11 and can be filled with an impact resistant padding material, or the housing can be made to abut the system electronics to eliminate or minimize the gap space. It its simplest form the core module 10 comprises just the system electronics 14 without a power supply, transducer, video interface or user interface. The core module 10 is highly mobile and very lightweight. The core module can be easily moved from place to place and mated to a modular ultrasound system 60 having the additional components desired for performing any variety of ultrasound scans.

The system electronics 14 (FIG. 1B) has one or more concatenated functions (filters) and includes a transmit/receive ASIC (beamformer) which are capable of driving one or more transducer arrays (not shown). The concatenated functions are ultrasound functions for processing signals in various ways. Two examples are a QBP filter and a digital Doppler processing function. The concatenated functions are not necessarily serially linked in that they require each other to operate. Though this is true in some cases where the processing of one type of signal is needed for the handling of another (e.g. QBP can be used by both a B mode and a PW Doppler mode), it is not necessary that a circuit for color power angio is linked together with continuous wave Doppler, in this instance, the filters can operate independently. The transmit/receive ASIC also controls the active transmit and receive apertures of a transducer array and the gain of the received echo signals. Echo data received by the transmit/receive ASIC are provided to the adjacent front end ASIC, which digitizes and beamforms the echoes from the individual transducer elements into coherent scan line signals. The front end ASIC also controls the transmit waveform timing, aperture and focusing of the ultrasound beam through control signals provided for by the transmit/receive ASIC. A memory device is connected to the front end ASIC which stores data used by the beamformer.

Figure 1B:
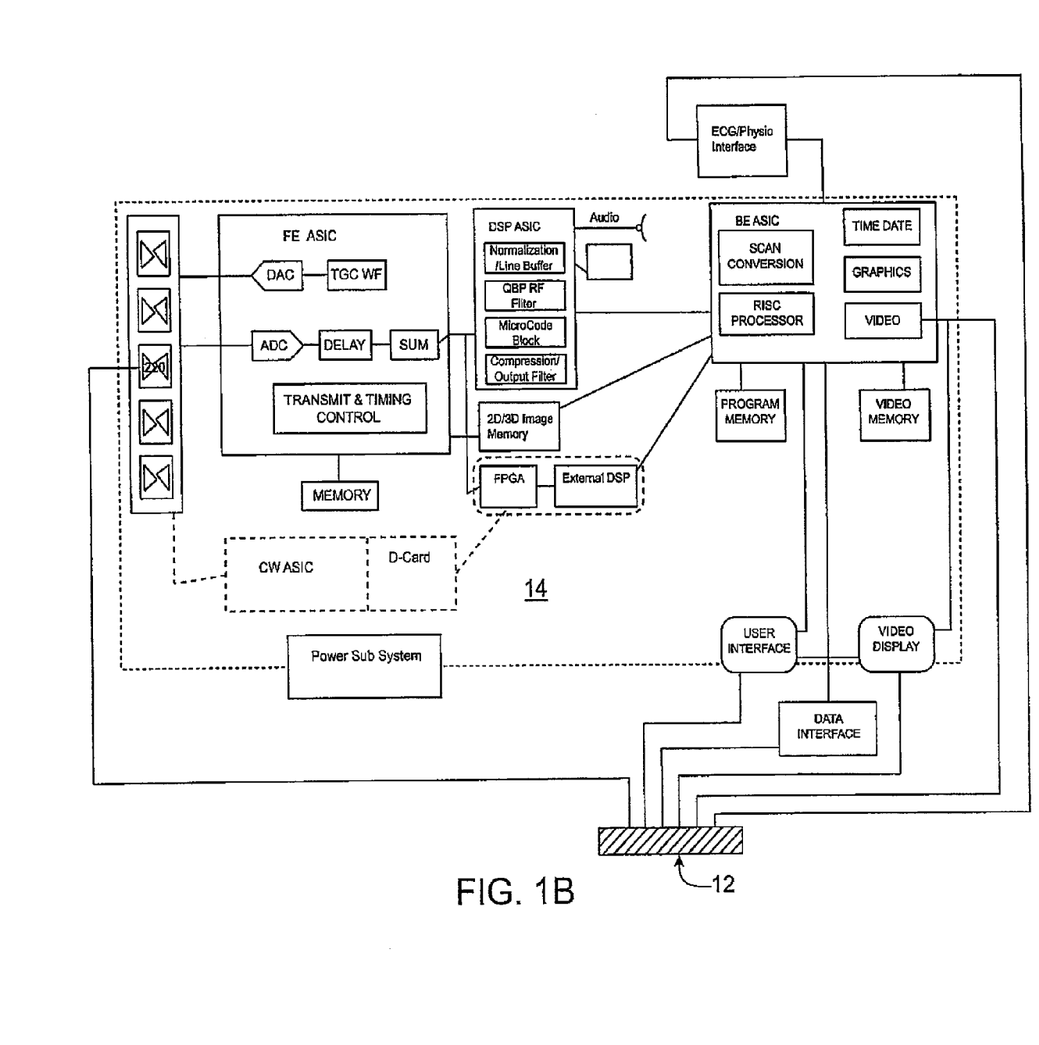
FIG. 1B shows a core unit module of the present invention.

The beamformed scan line signals are coupled from the front end ASIC to the adjacent digital signal processing ASIC. The digital signal processing ASIC filters the scan line signals and can provide additional features such as synthetic aperture formation, frequency compounding, Doppler processing such as power Doppler (color power angio) processing, speckle reduction, and pulse wave Doppler. Additional features such as continuous wave Doppler, can be incorporated into the system electronics if desired.

Figure 3A:
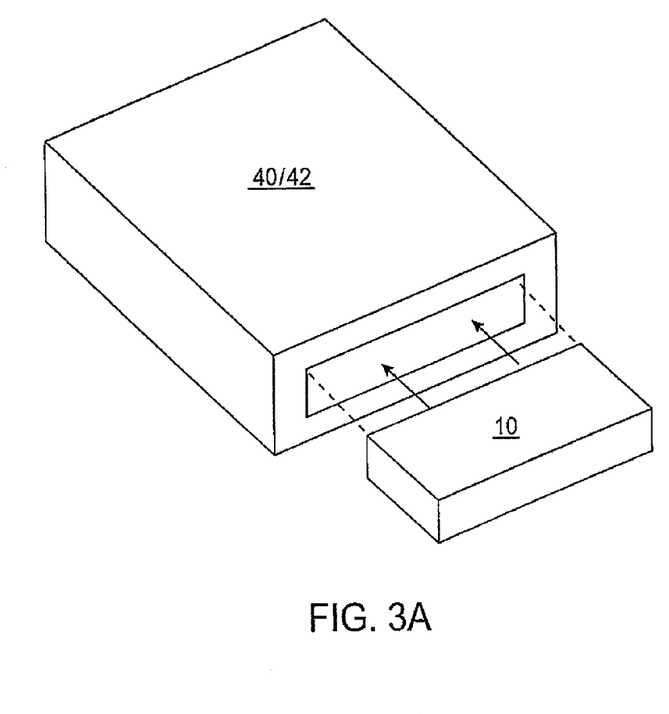
FIG. 3 shows a docking station style system module.
Figure 3B:
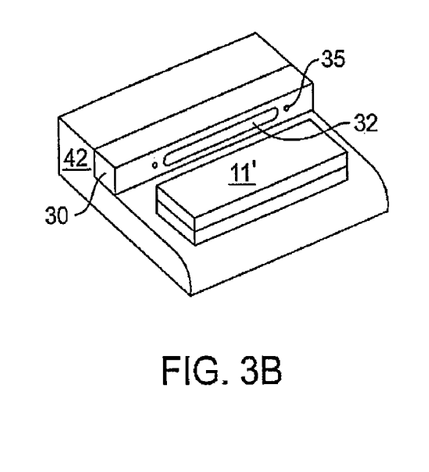

The ultrasound information is then coupled to the adjacent back end ASIC for scan conversion and the production of video outputs signals through the I/O port to the monitoring device attached to the core module. A memory device is coupled to the back end ASIC to provide storage used in three dimensional, 2D and power Doppler (3d CPA) imaging. The back end ASIC also adds alphanumeric information to the display such as the time, date, and patient identification. A graphics processor overlays the ultrasound image with information such as depth and focus markers and cursors. The graphics processor need not be incorporated into the core electronics system package, instead relying on a dedicated graphics processor card integrated into a docking module 40 of the modular system 60, and receiving the necessary component information from the core module 10. The video data can be transmitted through the I/O port 12 in one of several formats including NTSC, PAL, and RGB. Frames of ultrasound images are exported to an external video memory again through the I/O port 12 coupled to the back end ASIC. The stored data can be retrieved through the system electronics using a playback mode for either live Cineloop® real time sequence or as individual stills.

The back end ASIC also includes the central processor for the core module. The central processor is preferably a RISC (reduced instruction set controller) processor. The RISC processor is coupled to the front end and digital signal processing ASICs to control and synchronize the processing and control functions for both the core module, and the modular system the core module may be linked into at the time. A program memory is coupled to the back end ASIC to store program data which is used by the RISC processor to operate and control the core module, and the various elements of the modular system (transducer, multi-tap connector, video data overlay features, etc.). The RISC processor is also coupled to any user interface controls connected to the modular system, the RISC processor accepts user inputs to direct and control the operations of the core module, and the modular system as illustrated, all the inputs and outputs of the system electronics are designed to go through a single I/O port 12.

The main system, application and control software are stored in a persistent memory device integrated directly into the system electronics. The system software, control software and application software are loaded into the system electronics processors during power up. The core module may use any number of persistent memory devices integrated into the system electronics. Each ASIC includes a separate memory core having the necessary loadable data on it that is loaded into each ASIC during the power up cycle. The main system and application software includes the essential driver and communications information for the core module to communicate with, and control, a select number of peripherals. In particular these peripherals include scan heads, preferred user I/O devices (such as keyboards, pointer devices and touch screen interface recognition), printers, VCRs, monitors and data storage devices. The entire volume of system and application software should be efficiently coded to preserve space and avoid the need for a large capacity storage device like a hard drive. Since the core module is principally designed for diagnostic ultrasound, large capacity storage devices such as hard drives should not be necessary. The omission of devices like a hard drive, power supply and other elements commonly incorporated into computers or typical hand held products allows the core module to be manufactured with the smallest foot print the technology will allow. The housing for the core module only needs to securely enclose the system electronics and the I/O port. To improve impact resistance, the system electronics can be encased in resin or epoxy.

Power for the core module is provided by the modular system through the I/O port, or in the alternative, through a separate I/O used as a dedicated power terminal. Although the core module preferably does not have a built in power supply, it still requires a power monitoring/regulating circuit to provide proper power to the individual components during use. An external power supply can feed energy to the core module either through the I/O port, or through a dedicated power adaptor, however the power supply "brick" must be separate from the core module.

Figure 1C:
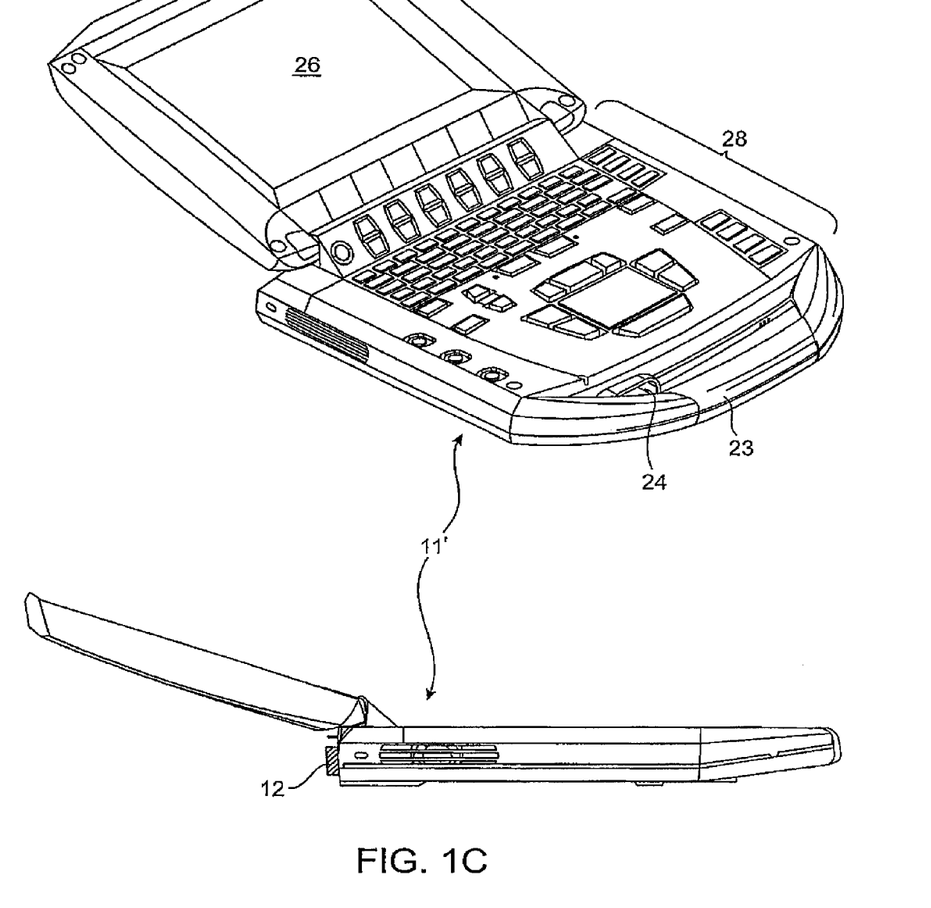
FIG. 1C shows a clamshell embodiment of the core unit.

In an alternative embodiment, the core module can incorporate additional hardware elements allowing the core module to operate as a stand alone device. In a first alternative embodiment, the core module 10 includes the features of previously described hand-held ultrasound systems in the form of system electronics, video out with the addition of an on board video display device 26, and a plurality of user inputs 28 in the form of a pointer, alphanumeric keypad, touch screen, programmable hot keys, and/or display control dials. This embodiment may also include speakers for audio output (not shown) and/or a direct transducer connection 24. The core module 10 now requires an internal power supply 25 in the form of a battery in order to operate as a stand alone device. This embodiment also requires either a built in or removable data storage device.

For ergonomic considerations, the stand alone version of the core module may be in the form of a tablet style PC or a laptop computer, as both of these designs are commonly used today and provide users with a familiar design and interface mode. In these embodiments the core module must have sufficient video capabilities to drive the video device coupled to the core module, such as an LCD device. The display out put can be as low as six bit to provide sufficient color capacity to drive the core module video display, or an external display that the core module may be attached to. The display output is preferably 8 or 16 bit, but can be include 24 bit RGB output. Color supporting bandwidth is necessary for some ultrasound scans that involve color display (PW, color angio) or higher definition gray scale. Where the core module 10 may be connected to a docking station 40 having an independent video processor, the data necessary for the video display need only be transmitted to the independent video processor. It is both possible and desirable in certain instances to be able to utilize both displays simultaneously, such as in the instances where more than one display is desired, or where it is necessary to check one display against the other as in a system diagnostic test.

In another variation on this embodiment, a form factor having the tablet or laptop configuration may include a built in handle 23. The handle 23 may be used strictly for carrying the core module 20, or it may serve as a sound chamber for speakers built into the handle. The handle may also serve as an I/O port for a dedicated connection, such as an external mouse, power adaptor or other user interface tool. In operation a user may use the handle as a wrist rest to reduce the incidence of repetitive motion syndrome while inputting information into the core module 10 through the user interface 28.

No matter what user interface elements are incorporated into the core module, the principle design is still focused toward, and optimized for, using the core module with a modular system. Thus while the core module may have the features of a portable or hand-held ultrasound system, it remains primarily the core module of a larger modular system that has greater capacity for complete diagnostic ultrasound scans with a full range of peripheral devices at the ready.

Figure 2:
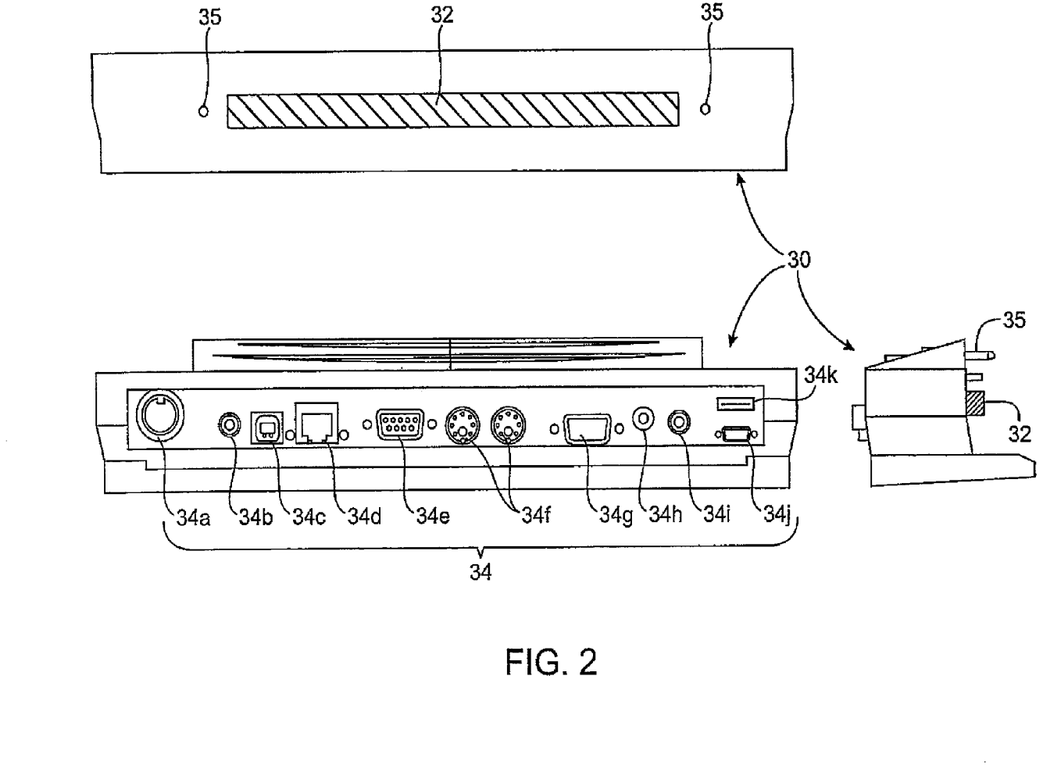
FIG. 2 shows a mini-dock style connector module.

The connection between the core module 10 and the modular system is through a receptacle module 30 or mini-dock. The receptacle module 30 connects peripheral devices to the core module 10. The receptacle module 30 comprises a receptacle housing, peripheral ports 34 and a receptacle 32. The receptacle module housing is a body designed to contain the hardware needed to provide the electronic communication between the peripheral devices and the core module 10. A plurality of peripheral device ports 34 are mounted in said receptacle housing 30, each peripheral device port is connected to one or more individual electrical connector(s) for electrical communication with a receptacle 32. The receptacle 32 is designed for releasably mating with the I/O port 12 of the core module 10. Thus the core module 10 may communicate with the desired peripheral devices through the receptacle module, and visa-versa.

The electronic communication between said receptacle 32 and the plurality of peripheral device ports 34 can be either a pass through connection or an active connection. If the connection is active, the receptacle module 30 contains one or more active circuits. The interface functions essentially as an interface converter for signals. Typically the active circuits required are analog to digital (A/D) and digital to analog (D/A) converts for video out and in. It may also perform digital-to-digital conversion (D/D) for different digital video outputs. By placing the A/D and D/A converters in the receptacle housing 30, space and weight is conserved within the core module 10. This provides a substantial weight and real estate savings in the core module 10 whether it is used as a stand alone unit, or as a central processing core for a modular system. Video A/D and D/A converters should not be needed in the core module having built in video, since the built in display should be able to use the native signal without conversion.

Figure 4:
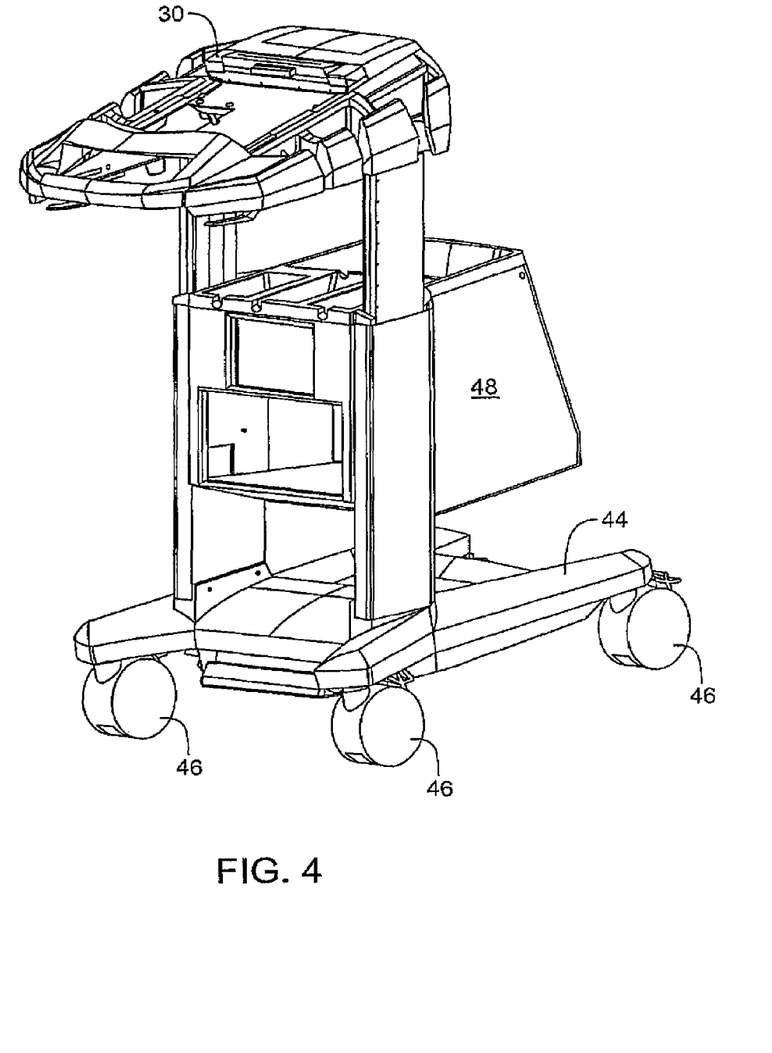
FIG. 4 shows a mobile workstation style system module.

The receptacle housing may also have a latching mechanism 35 for securing itself to the core module 10. A simple latch, such as tension locking arms or hooks may be used, or an interlocking connector like rails and grooves. A manual release of the interlocking mechanism allows for an easy release of the core module and the receptacle module. This feature may be found in another module when the receptacle module 30 is connected to either a docking station 40 or a mobile docking stand 50. The receptacle housing itself contains all the connectors needed for the core unit to interface with a wide body of peripheral devices. Examples of such connections include specialized adaptors for power 34a, printer 34b, network 34c, Ethernet 34d, RS232 adaptor 34e, S-video out 34f, VGA out 34g, composite video out 34h, sound out 34i, physio-adaptor 34j (as for an ECG measuring device), and transducer adaptor 34k. The physio port is designed for receiving input from a device that measures some physiological parameter that a user can combine with a diagnostic ultrasound scan to produce a more accurate diagnosis. Electro cardio gram (ECG) measurements are an example of such a physio-monitoring device that can be used in conjunction with the ultrasound scan. Additional controls for a full sized user interface station (keyboard, pointer, input devices) may use an additional port, or go through the Ethernet adaptor 34d or RS232 34e port. The peripheral devices are "off the shelf" materials commonly used in hospitals and ultrasound scanning environments, and the receptacle housing uses peripheral ports to match these existing technologies. However the receptacle module can be constructed and configured to communicate with virtually any device so long as the system electronics 14 has the appropriate communications protocol programmed into it. The receptacle housing may further include a surge protector (not shown) to shield the core module from electrical surges while plugged into a power supply.

The receptacle housing uses a plurality of electrical pins in the receptacle 32 for communication with the I/O port 12 of the core module 10. The layout of the pins varies with the intended communication the core module would need to interact with a modular system, or a series of stand alone peripherals. Further pin economy may be achieved by using the same pins for communicating to different devices through a well timed cycle of instructions based on the system clock, such as with an I2C protocol. An example of the pin layout is as follows:

PINS 1-20 Power and ground
PINS 21-106 Digital video out
PINS 107-143 Communication links, (e.g. RS232, Ethernet, USB printer, I2C, ECG and Audio in/out.
PINS 144-200 Connection status lines, additional ground lines, and spare lines.

In a fourth embodiment of the present invention, a docking station 40 is designed to mate with the core module 10 through a receptacle module 30. The docking station 40 is used for connecting a plurality of peripheral devices to the core module. The docking station 40 comprising a receptacle module 30 component as described above attached to a base unit 42. The base unit 42 has a means for guiding the core module 10 into alignment with the receptacle module 30. The base 42 also preferably includes a means for securing the core module and the receptacle module into place while connected. The means for guiding the core module into place and securing the core module into position can be the same feature. By way of example, the docking station may include a mechanical tray or cradle having an open position that the core module can be placed into, then the mechanical tray or cradle is moved to a closed position with the core module in place. The movement of the mechanical tray or cradle causes the core module to be moved into the proper position and locked into position at the same time. As long as the mechanical tray or cradle is in place, the core module cannot be removed or become misaligned. The mechanism could be a simple funnel type of guide rails that ensure the core module is funneled into the correct orientation for proper docking. The user in this case must apply the necessary force to ensure the core module and receptacle module or docking station properly line up. An electromechanical device may also be used. A small motor could be used to perform the mechanical work of a person, and the motor could be activated as soon as it detects the core module in place, or by the push of a button from a user. The docking station incorporates a power supply within the base and in electronic communication with the receptacle module such that electrical power can be fed from the power supply to the core module through the receptacle module/mini-dock.

Alternatively the docking station may utilize a housing having a slot or aperture for slidably receiving the core module. Thus in a fashion similar to the way a VHS tape is inserted into a VCR, the core module would be placed into the docking station having a housing, and an electromechanical component would draw the core module into the housing and secure it in place. In this embodiment the housing can be either attached to the base, or incorporate the base into a single component. In this embodiment it is not possible to utilize and video display which may be incorporated into the core module, therefore it would be preferable to reinforce the internal frame of the housing to support the weight of a video display, such as a CRT, LCD or plasma display monitor.

In either format, the docking station would not be mobile, so the use of additional accessories that ordinarily would not be considered highly portable is logistically acceptable here. Such additional components include a larger, more ergonomically designed user interface, such as a full size QWERTY style keyboard, a pointing device such as a mouse, track ball or "joy stick." A large touch screen can also be used to allow the use of on screen hot keys and supplemental pointer device.

Figure 5:
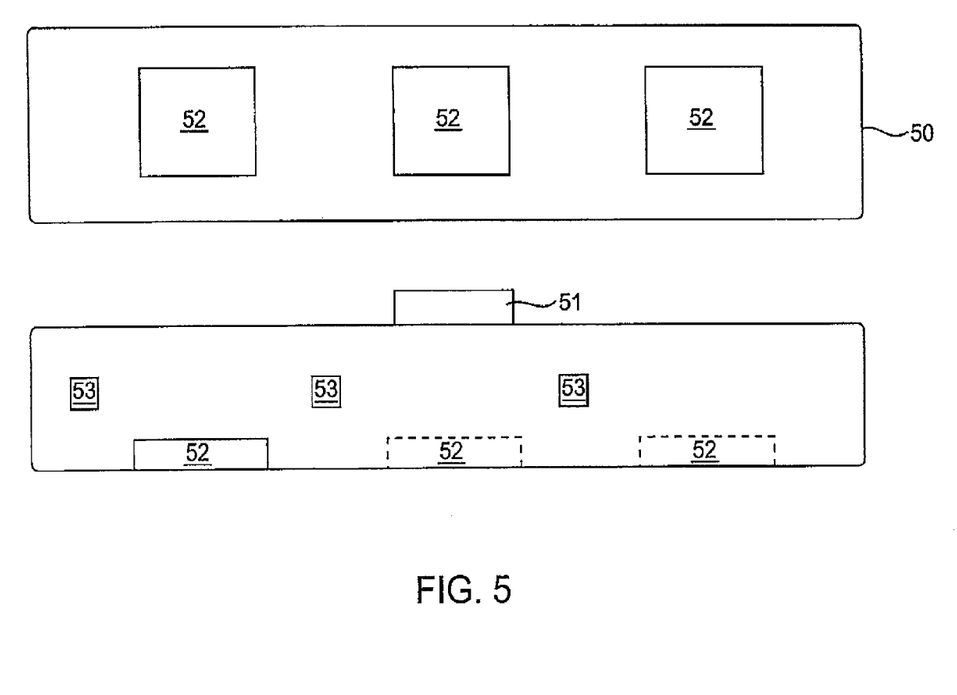
FIG. 5 shows a multi-tap transducer module.

A fifth module for use with the docking station is a multi-transducer interface module 50. The multi-transducer interface module 50 has a single transducer connector 51 for mating with the docking station 40, or in the alternative with the transducer connector aperture 24 of the core module, and a plurality of transducer connector apertures 52 incorporated into the multi-tap module. In this manner the docking station 40 can have at the ready a variety of ultrasound probes, such as a neonatal probe, trans-esophageal probe, or any other probe desired to be used in a diagnostic scan. When the core module 10 is mated to the docking station 40 and powered up, the core module 10 can detect which transducers are connected to the system and select the appropriate beamformer program and data processing to match the probe. The multi-tap module 50 may incorporate either a plurality of electromechanical switches 53 to allow a user to switch between probes, of the core module 10 may contain a soft switch within its system electronics package to switch between transducers at the direction of a user.

Additional utility is realized in a sixth embodiment in the form of a mobile docking station 45. The mobile docking station 45 comprises a base 44 having a plurality of castors 46 wherein at least one said castor is capable of locking, a tower 48 is mounted on the base and a docking station 40 is located substantially near the top of the tower 48, the docking station 40 is capable of releasably receiving the core module 10.

The mobile docking station 45 can incorporate a plurality of storage bins into the tower design. The bins can be used for the storage of both peripheral devices such as a printer, data storage device and VCR, as well as peripheral equipment such as coupling gels, transducers, connecting cables and the like. The tower is preferably height adjustable and may include gas cylinders actuated by a manual trigger to raise or lower the docking station. The tower is preferably a weight balanced design to avoid imbalance of the mobile docking station either while in use, or while being moved from place to place. The tower may be any design corresponding to the weight balanced design, such as an "A" frame, "Z" frame, an inverted "T" frame, or an "I" frame. Multiple other frames are equally usable assuming the base has been weighted to compensate for the positioning of peripheral devices and accessory products that might be used in the ordinary course of the mobile docking station.

Similar in the design and intended use of the stationary docking station, the mobile docking station can incorporate the interface to the core module for a multi-transducer adaptor (multi-tap module) and an enhanced user interface utilizing full sized components for ease of use.

Figure 6:
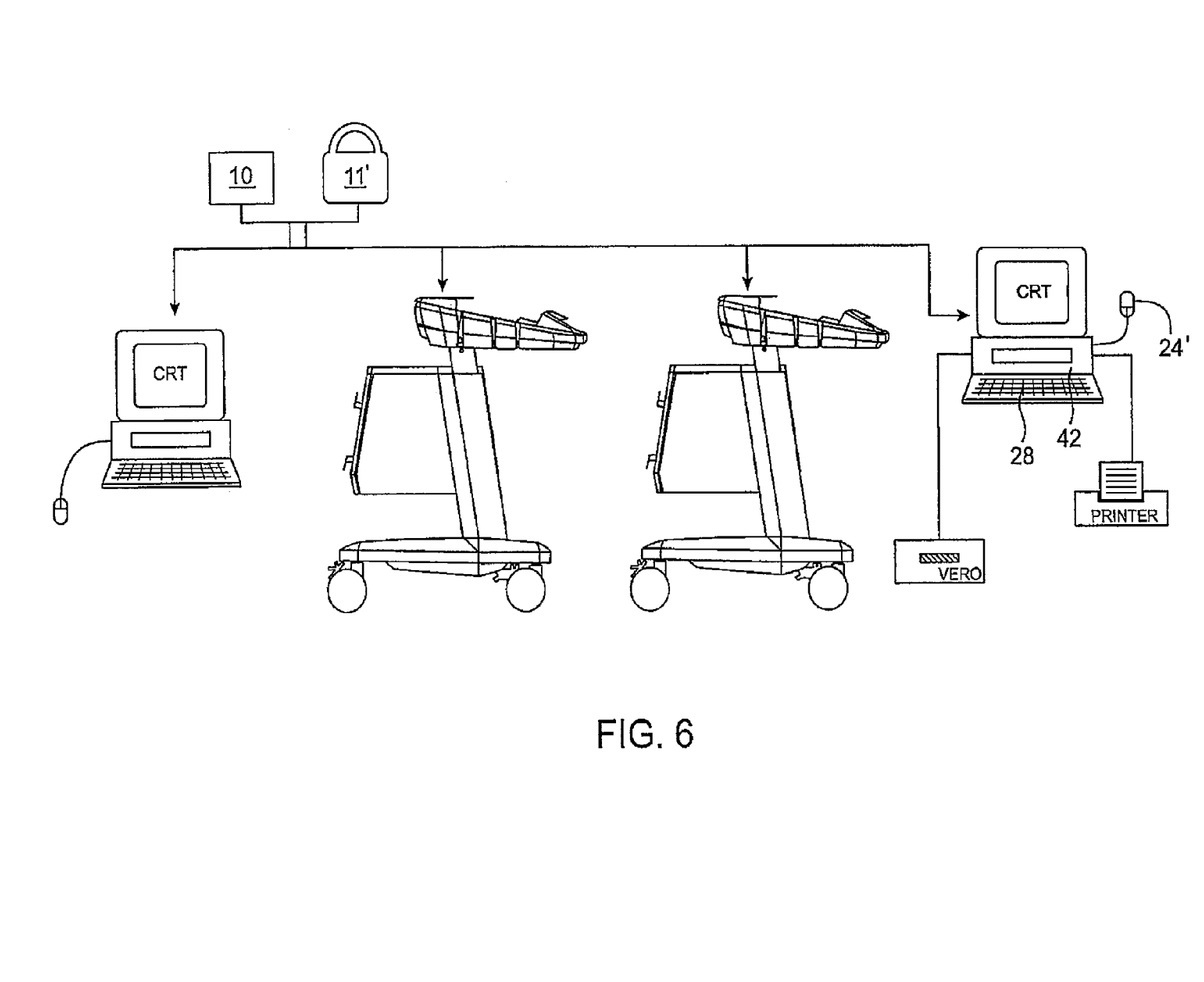
FIG. 6 shows a multi station system incorporating all the modules.

In another embodiment of the present invention, a system 60 is envisioned for providing enhanced diagnostic ultrasound flexibility and capacity through the use of one or more core modules 10 and a plurality of docking stations 40. The docking stations may either be desktop (stationary 40) or mobile 45 in design. In this manner, a user, such as a hospital or clinic can reduce the costs of purchasing a variety of ultrasound devices, and instead purchase a multitude of cheaper docking stations 40 or mobile docking stations 45. It can be appreciated by those who perform ultrasound scans that there is an advantage for only paying for expensive equipment such as the core module once or twice, and being able to carry that around easily and using it with cheaper docking stations or mobile docking stations. Substantial savings in capital equipment may be made in using a system of this design. The alternative embodiment of the core module 10 which incorporates hand held functionality can then operate as a mobile or field device and then return to a docking station for operation with a plurality of peripheral devices, thus enabling the mobile unit to perform as a the processor for an ultrasound suite. The core module 10 is designed to provide complex ultrasound capabilities such as those found in large, premium devices, as well as scaled down feature sets in the event it is plugged into a dock with less capable peripherals. The core module is fairly simple in construction, yet provides the processing for as many ultrasound features as a user may desire. The core may be easily and quickly removed from one dock and inserted into another, even if the docking station is "hot" (powered).

Where the core module is moved from one docking station to another within system 60, the system electronics package has the capability to either automatically detect, or identify through user input, the type of ultrasound probe attached to the docking station it is being used with, and draw on the appropriate concatenated filters needed. This allows maximum flexibility and minimum user effort in the system.

While the descriptions above provide a sense of the invention, the full scope of the invention is more accurately provided in the appended claims.

What is claimed is:

1. A mini-dock for connecting peripheral devices to a modular diagnostic ultrasound apparatus, the mini-dock comprising:
   a receptacle housing;
   a plurality of peripheral device ports, in or on said receptacle housing, each peripheral device port connected to one or more individual electrical connector(s), at least one peripheral device port of said plurality of peripheral device ports comprises an ultrasound transducer adaptor; and
   a receptacle for releasably mating with an I/O port of said modular diagnostic ultrasound apparatus, said receptacle in electronic communication with said plurality of peripheral device ports.

2. The mini-dock as described in claim 1, wherein the electronic communication between said receptacle and said peripheral device ports is a pass through connection.

3. The mini-dock as described in claim 1, wherein the electronic communication between said receptacle and said peripheral device ports is achieved through the use of one or more active circuits.

4. The mini-dock as described in claim 3, wherein an active circuit of the one or more active circuits is a digital to analog video converter for video signal passing from the modular diagnostic ultrasound apparatus to a video device through a peripheral device port.

5. The mini-dock as described in claim 3, wherein an active circuit of the one or more active circuits is an analog to digital video converter for video feed through a peripheral device port to the receptacle.

6. The mini-dock as described in claim 1, having one or more means for removably connecting the mini-dock to the modular diagnostic ultrasound apparatus.

7. The mini-dock as described in claim 1, further comprising a surge protector.

8. The mini-dock as described in claim 1, wherein at least one peripheral device port of said plurality of peripheral device ports comprises a physio-adaptor.

9. A docking station for connecting a plurality of peripheral devices to a modular diagnostic ultrasound apparatus, the docking station comprising:
  a mini-dock having a housing, a receptacle, a plurality of peripheral device ports in electronic communication with the receptacle, at least one peripheral device port of said plurality of peripheral device ports comprises an ultrasound transducer adaptor;
  a base fixedly attached to the mini-dock and having means for guiding a modular diagnostic ultrasound apparatus into alignment with said mini-dock and means for securing the modular diagnostic ultrasound apparatus to the mini-dock; and
  a power supply incorporated within said base and in electronic communication with said mini-dock such that electrical power can be fed from the power supply to the modular ultrasound apparatus through the mini-dock.

10. The docking station as described in claim 9, wherein the base further comprises a housing having an aperture for slidably receiving said modular diagnostic ultrasound apparatus.

11. The docking station as described in claim 10, wherein said housing has a reinforced internal frame for supporting a video display unit.

12. The docking station as described in claim 9, further comprising a plurality of user interfaces for controlling said modular diagnostic ultrasound apparatus.

13. A multi-transducer connector module comprising a housing having a relief connector for mating with an aperture for a transducer connector on a modular diagnostic ultrasound apparatus, said multi-transducer connector having a plurality of recess connectors fittingly engaging a plurality of relief transducer connectors of a plurality of diagnostic ultrasound transducer assemblies, the housing having a switch for each recess connector by which an operator can select which transducer connected to the ultrasound device to be used at any particular moment.

14. The multi-transducer connector of claim 13, wherein the switch is an electronic switch controlled through a user interface.

15. The multi-transducer connector as described in claim 13, wherein the various transducers of the plurality of diagnostic ultrasound transducer assemblies may be hot switched for use with said modular diagnostic ultrasound apparatus.

16. The multiple transducer connector of claim 13, wherein when the diagnostic ultrasound apparatus is operable to detect which transducers are connected to the multi-transducer connector for selection of appropriate beamformer program and data processing functionality when the diagnostic ultrasound apparatus is mated to the multi-transducer connector.

17. A mobile docking station for use with a modular diagnostic ultrasound apparatus comprising:
  a base having a plurality of castors wherein at least one said castor is capable of locking;
  a tower mounted on said base; and
  a docking station located substantially near the top of the tower, the docking station capable of releasably receiving a modular diagnostic ultrasound apparatus, said docking station having a plurality of peripheral device ports, each peripheral device port connected to one or more individual electrical connector(s), at least one peripheral device port of said plurality of peripheral device ports comprises an ultrasound transducer adaptor, and a receptacle for releasably mating with an I/O port of said modular diagnostic ultrasound apparatus, said receptacle in electronic communication with said plurality of peripheral device ports.

18. The mobile docking station as described in claim 17, further comprising a plurality of storage bins.

19. The mobile docking station as described in claim 17, wherein the tower further comprises a means for adjusting the height of the tower.

20. The mobile docking station as described in claim 19, wherein the means for adjusting the height of the tower is a gas cylinder actuated by a manual trigger.

21. The mobile docking station as described in claim 17, wherein the tower is a Z frame.

22. The mobile docking station as described in claim 17, wherein the tower is a A frame.

23. The mobile docking station as described in claim 17, wherein the tower is an inverted T frame.

24. The mobile docking station as described in claim 17, wherein the tower is an I frame.

25. The mobile docking station as described in claim 17, wherein said plurality of peripheral device ports of said docking station further comprises an I/O port operable for connecting a universal control pad.

26. A system for diagnostic ultrasound examinations comprising:
  at least one core module having a housing, system electronics package and a I/O port; and
  one or more docking station(s) in electronic communication with a plurality of peripheral devices, the docking station capable of releasable connection to said core module, wherein the core module is operable to generate diagnostic ultrasound images while docked to at least one docking station of the one or more docking station(s), and said core module further operable so that all data inputs and outputs are sent or received through the at least one docking station to or from the peripheral devices.

27. The system of claim 26, wherein the docking station is a mobile docking station.

28. The system of claim 26, wherein the one or more docking station(s) is a mix of mobile docking stations and desktop docking stations.

* * * * *

UNITED STATES PATENT AND TRADEMARK OFFICE
CERTIFICATE OF CORRECTION

PATENT NO. : 7,591,786 B2  Page 1 of 1
APPLICATION NO. : 10/356401
DATED : September 22, 2009
INVENTOR(S) : Holmberg et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1324 days.

Signed and Sealed this

Twenty-first Day of September, 2010

David J. Kappos
*Director of the United States Patent and Trademark Office*